(12) United States Patent
Rosenblatt

(10) Patent No.: US 10,973,432 B2
(45) Date of Patent: Apr. 13, 2021

(54) ELECTRICAL DETECTION OF ANATOMIC WALL PENETRATION AND DELINEATION OF ANATOMIC STRUCTURES DURING SURGERY

(71) Applicant: Rosenblatt Associates, LLC, West Newton, MA (US)

(72) Inventor: Peter L. Rosenblatt, West Newton, MA (US)

(73) Assignee: Rosenblatt Associates, LLC, West Newton, MA (US)

( * ) Notice: Subject to any disclaimer, the term of this patent is extended or adjusted under 35 U.S.C. 154(b) by 197 days.

(21) Appl. No.: 16/222,525

(22) Filed: Dec. 17, 2018

(65) Prior Publication Data

US 2019/0183377 A1 Jun. 20, 2019

Related U.S. Application Data

(60) Provisional application No. 62/708,682, filed on Dec. 18, 2017.

(51) Int. Cl.

| | |
|---|---|
| A61B 5/053 | (2021.01) |
| A61B 5/0538 | (2021.01) |
| A61B 5/00 | (2006.01) |
| A61L 29/10 | (2006.01) |
| A61L 29/14 | (2006.01) |
| A61B 1/06 | (2006.01) |
| A61B 17/04 | (2006.01) |
| A61F 6/04 | (2006.01) |
| A61B 90/00 | (2016.01) |
| A61B 34/30 | (2016.01) |
| A61B 1/303 | (2006.01) |
| A61B 17/00 | (2006.01) |

(52) U.S. Cl.
CPC .......... *A61B 5/0538* (2013.01); *A61B 1/0661* (2013.01); *A61B 5/4337* (2013.01); *A61B 5/6852* (2013.01); *A61B 5/742* (2013.01); *A61B 5/7405* (2013.01); *A61B 5/7455* (2013.01); *A61B 17/0469* (2013.01); *A61L 29/106* (2013.01); *A61L 29/14* (2013.01); *A61B 1/303* (2013.01); *A61B 2017/00026* (2013.01); *A61B 2034/302* (2016.02); *A61B 2090/0801* (2016.02); *A61B 2090/08021* (2016.02); *A61B 2505/05* (2013.01); *A61F 6/04* (2013.01)

(58) Field of Classification Search
CPC ... A61B 5/0538; A61B 5/6852; A61B 5/7405; A61B 5/742; A61B 5/4337; A61L 29/106; A61L 29/14

See application file for complete search history.

(56) References Cited

U.S. PATENT DOCUMENTS

| | | |
|---|---|---|
| 3,791,385 A | 2/1974 | Davis et al. |
| 4,909,263 A | 3/1990 | Norris |
| 5,209,754 A | 5/1993 | Ahluwalia |

(Continued)

OTHER PUBLICATIONS

International Search Report and Written Opinion for PCT/US2008/086632 dated Jun. 24, 2009.

*Primary Examiner* — Richard G Louis
(74) *Attorney, Agent, or Firm* — Foley Hoag LLP; Rajesh Vallabh

(57) ABSTRACT

Devices and methods are disclosed that detect and/or prevent intraoperative full thickness penetration of anatomic walls and provide delineation of anatomic structures during surgery.

20 Claims, 2 Drawing Sheets

(56) References Cited

U.S. PATENT DOCUMENTS

| | | | |
|---|---|---|---|
| 5,301,658 A | | 4/1994 | Zhu et al. |
| 5,578,048 A | | 11/1996 | Pasqualucci et al. |
| 5,643,285 A | | 7/1997 | Rowden et al. |
| 5,746,224 A | | 5/1998 | Edwards |
| 6,081,749 A | | 6/2000 | Ingle et al. |
| 6,210,314 B1 | | 4/2001 | Ein-Gal |
| 6,423,075 B1 | | 7/2002 | Singh et al. |
| 6,546,934 B1 | | 4/2003 | Ingle et al. |
| 6,558,381 B2 | | 5/2003 | Ingle et al. |
| 6,625,495 B1 | | 9/2003 | Alon et al. |
| 6,629,535 B2 | | 10/2003 | Ingle et al. |
| 6,709,380 B2 | | 3/2004 | Green et al. |
| 6,912,416 B2 | | 6/2005 | Rosenblatt |
| 7,079,882 B1 | | 7/2006 | Schmidt |
| 7,722,538 B2 | | 5/2010 | Khoury |
| 8,079,963 B2 | | 12/2011 | Rosenblatt |
| 2001/0018606 A1 | | 8/2001 | Ingle et al. |
| 2003/0125787 A1 | * | 7/2003 | Shchervinsky ...... A61N 1/0595 607/132 |
| 2003/0178032 A1 | | 9/2003 | Ingle et al. |
| 2005/0085827 A1 | | 4/2005 | G. et al. |
| 2010/0179632 A1 | * | 7/2010 | Bruszewski ....... A61B 18/1492 623/1.11 |
| 2010/0286482 A1 | * | 11/2010 | Rosenblatt ........... A61B 5/0538 600/202 |

* cited by examiner

ELECTRICAL DETECTION OF ANATOMIC WALL PENETRATION AND DELINEATION OF ANATOMIC STRUCTURES DURING SURGERY

CROSS-REFERENCE TO RELATED APPLICATION

This application claims priority from U.S. Provisional Patent Application No. 62/708,682 filed on Dec. 18, 2017 entitled ELECTRICAL DETECTION OF ANATOMIC WALL PENETRATION AND DELINEATION OF ANATOMIC STRUCTURES DURING SURGERY, which is hereby incorporated by reference.

BACKGROUND

Pelvic reconstructive surgery often involves placing sutures into endopelvic fascia. These procedures can be performed abdominally or laparoscopically/robotically. For the purposes of this discussion, a laparoscopic approach will be described, but it should be understood that these principles may apply to abdominal and robotic surgery as well. Procedures that are used for reconstructive pelvic surgery include uterosacral ligament suspension, paravaginal repair, Burch colposuspension, sacrocolpopexy, and sacrocervicopexy. When performing these procedures, most surgeons prefer to avoid penetration of the vaginal lumen. This is especially true when mesh is used for reconstructive surgery. Suture penetration may increase the risk of mesh erosion. Some surgeons place a hand in the vagina in an attempt to avoid vaginal penetration. Other surgeons use vaginal probes, Lucite molds or end-to-end anastomotic (EEA) sizers placed in the vagina and suturing is performed over these devices. More recently, robotic surgery has been used in gynecologic reconstructive surgery, which deprives the surgeon of the tactile sensation that can be used to avoid vaginal penetration of suture material. In addition, the bladder and rectum are adjoining structures that may be injured during suturing in the endopelvic fascia. Most surgeons use vaginal probes that are essentially cylindrical, elongated solid devices with a rounded tip. Some probes, such as the vaginal probe from Apple Medical, and the EEA sizers, have a distal end with a defined diameter that is attached to a handle by a narrow rod.

SUMMARY

The disclosed devices and methods in accordance with various embodiments may be employed to detect and/or prevent intraoperative full thickness penetration of anatomic walls, and to provide delineation of anatomic structures during surgery. For example, a probe that is shaped to conform to an anatomic structure is placed in that anatomic structure. The probe has a conductive surface and is electrically connected to an electrical meter. Since body tissues also conduct electrical current, the probe has a non-conductive covering (e.g., a coating or a sleeve similar to a latex condom or glove) that will not complete the electrical circuit unless the covering is perforated with a needle or other sharp surgical tool. A needle or other penetrative device for surgical use is also electrically connected to the electrical meter. A source of electricity (such as a battery) is electrically connected to at least one of the probe, penetrative device, and meter. The probe, penetrative device, meter, electricity source, and electrical connections therebetween form an electrical circuit if the probe and penetrative device become electrically connected, such as by full-thickness penetration of the penetrative device through the wall of the anatomic structure so that the sharp needle or other instrument breaks the non-conductive material and contacts the probe. A surgeon operating adjacent the anatomic structure with the needle or other penetrative device thus can be alerted when the wall is penetrated and adjust the surgical technique accordingly. Examples of anatomic structures include hollow organs, such as blood vessels, airways, esophagus, stomach, small intestine, large intestine, uterus, vagina, ureter, bladder, and urethra.

A probe, by conforming to an anatomic structure, can help delineate that structure to facilitate its identification and positioning during a surgical procedure.

DETAILED DESCRIPTION

Figure 1:
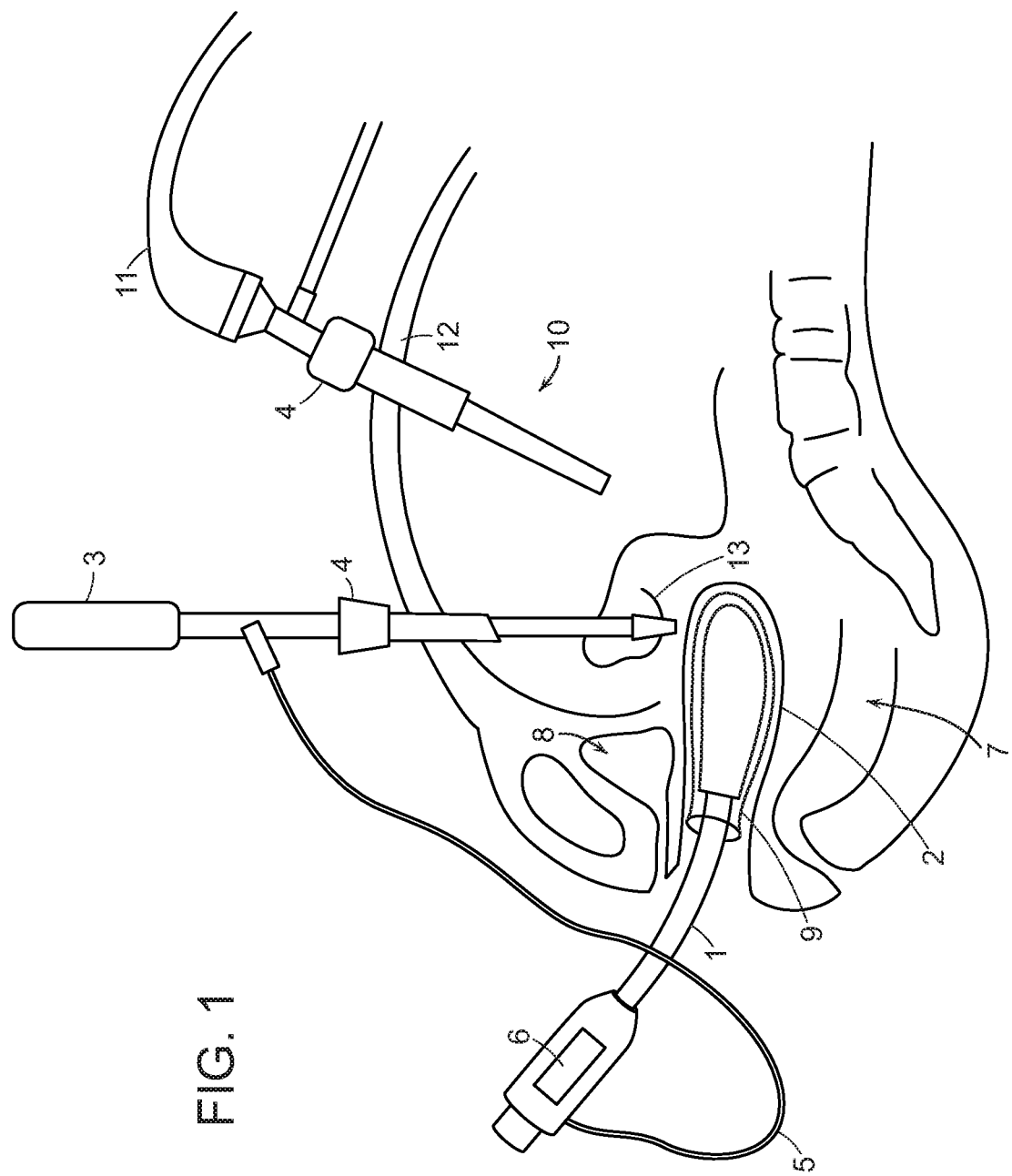
FIG. 1 shows a schematic of an exemplary electrical tissue injury detection system in accordance with one or more embodiments, including an electrical device that provides a source of electricity through the circuit created by a penetrative device, such as a suture needle, and a conductive probe placed, e.g., in the vagina, which has a non-conductive material covering the device (e.g., a coating or a sleeve like a latex glove or condom). The meter in the device, such as an ammeter, measures an electrical property of the system, such as the current in the circuit, and the resistance may thus be calculated to determine whether penetration of the vagina and non-conductive material with the suture needle has occurred.

An electrical system may be used for measurement of current in a circuit to rule in or out inadvertent vaginal, bladder, or rectal injury during reconstructive pelvic surgery, or injury to other organs during other types of surgery. Probes for anatomical structures may be used to delineate the structures to facilitate proper identification and suturing of tissues. Probes may be fixed to a stable structure, such as an operating table or to one another.

Although the subject matter is exemplified primarily in the context of electrical detection of vaginal penetration and delineation of pelvic structures during vaginal surgery, it is relevant in other contexts, such as surgery adjacent other hollow organs.

In one embodiment, two conductors are used, one located on a probe placed in the vagina, and the other being a needle attached to a needle driver. A power source (e.g., a battery) is connected to either the metallic probe in the vagina or the needle to power the system. The metallic tip of the probe is covered by a pierceable non-conducting material so that the electrical circuit is not complete, since body tissues may also conduct an electrical current. If the needle has penetrated the vagina and the non-conductive material covering the probe tip, a circuit will be completed wherein current may be measured, and wherein resistance will be minimal. Alternatively, if the needle has not entered the vagina, the resistance provided by the vaginal wall and the non-conductive material covering the metallic probe tip will prevent the circuit from being completed. With the application of a source of electricity to either the probe or the needle, no current will be detected. With direct current, it is known that Voltage=Current×Resistance. An electricity source may be positioned in the circuit to provide a current or a voltage across the circuit. For example, a voltage may be applied to the circuit (e.g., using a battery) and the current may be measured with an ammeter. In this manner, the resistance can be easily calculated, to determine whether or not the needle has penetrated the vagina. Alternatively, one may put out a fixed current and measure voltage, to determine resistance. In any event, the current measured would depend on the resistance in the tissues. The differences in resistance would be used to differentiate between a needle placed completely through the vagina and a properly placed needle in the endopelvic fascia without vaginal penetration. The same principles apply to a probe placed in the rectum, in order to prevent rectal injury. If vaginal or rectal penetration has occurred, the needle may be withdrawn and replaced. Alternatively, the rectal probe could be lighted (with either an external light source with a cord that would be attached to the bowel probe, or with an internal light source that is battery operated). The electricity source could be positioned, e.g., inside a probe or otherwise integrated with a probe, or integrated with another component in the circuit, or provided separately.

The pierceable non-conducting material covering the electrically conducive surface of the probe can comprise a variety of electrical insulator materials including, e.g., Latex (natural rubber), Santoprene (synthetic rubber—non-latex, hypoallergenic), Neoprene (synthetic rubber), and Silicone. In one or more embodiments, the non-conducting material can be in the form of a sleeve (e.g., a condom or condom like sleeve) fitted over the tip of the probe. In one or more embodiments, the non-conducting material can be a coating applied over the tip of the probe.

The electrical device may put out a fixed voltage, an ammeter measures current through the circuit, and disposable wires connect to the needle driver and vaginal probe.

The handle and shaft of the probe instrument may have a non-conductive surface, such as plastic, so that these components of the probe will not conduct an electrical current through the patient's tissues, with the non-conductive sleeve covering only the metallic probe tip, or the condom sleeve may cover the entire instrument, so that it will only conduct an electrical current when the covering is violated with a sharp instrument, such as a needle.

The handle and potentially the shaft of the instrument may be disposable and may have a compartment that houses the batteries, as well as electrical components of the ammeter, with an electrical connection to the distal probe (the part that conforms to the shape and size of the body cavity, such as the vagina, in the current example). The distal probes may come in several sizes and may be reusable, so that the surgeon may choose from one of several sizes and may affix (such as snap or otherwise attach) the distal probe to the disposable handle. In that manner, if the size is incorrect, the surgeon may choose a different distal metallic probe and the used probes may be re-sterilized.

The device may have an indicator, which may be auditory (such as a buzzer) or visual (such as a light) either on the handle, shaft, or somewhere along the wire that attaches to the needle driver, that signals when the vaginal wall or other structure has been perforated.

The device may have a handle located at the proximal end that may have the ability to flex and therefore antevert or retrovert the vaginal access. The probe may also have the ability to light up, in order to differentiate between the vagina and surrounding structures such as the bladder and rectum.

Delineation of the rectum may be accomplished with a solid probe, which may be oval shaped and may be lighted in order to identify the location of the rectum. The rectal probe may also have the ability to conduct an electrical current in order to identify needle perforation into the rectum, as described previously. The probe may have a handle that also allows deviation of the rectum either anterior, posteriorly or laterally.

For clarity and convenience, a number of exemplary embodiments will be described relating to a particular anatomic site, the female pelvis. However, it will be readily apparent to one of ordinary skill in the art that the disclosed systems and methods may be employed in a wide variety of anatomical settings to treat a broad range of abnormalities.

FIG. 1 illustrates the general design of an exemplary electrical tissue injury detection system in accordance with one or more embodiments. The system includes a probe (1) placed in some hollow organ, such as the vagina (2), covered by a non-conductive sleeve (9) and connected to an instrument, such as a laparoscopic needle driver (3), which has been placed through a trocar (4). A needle (13) is attached to the needle driver. The needle driver and probe are connected by conductive wires (5) and attached to an ammeter (6) so that a determination by electrical conductance can be made that will inform the surgeon with a signal (e.g., an auditory, tactile, and/or visual signal) whether or not the needle has penetrated the vagina and made contact with the probe. In this figure, the rectum (7) and the bladder (8) are located adjacent to the vagina. A laparoscope (10) with camera (11) is placed in this figure through another trocar (4) in the umbilicus (12).

Figure 2:
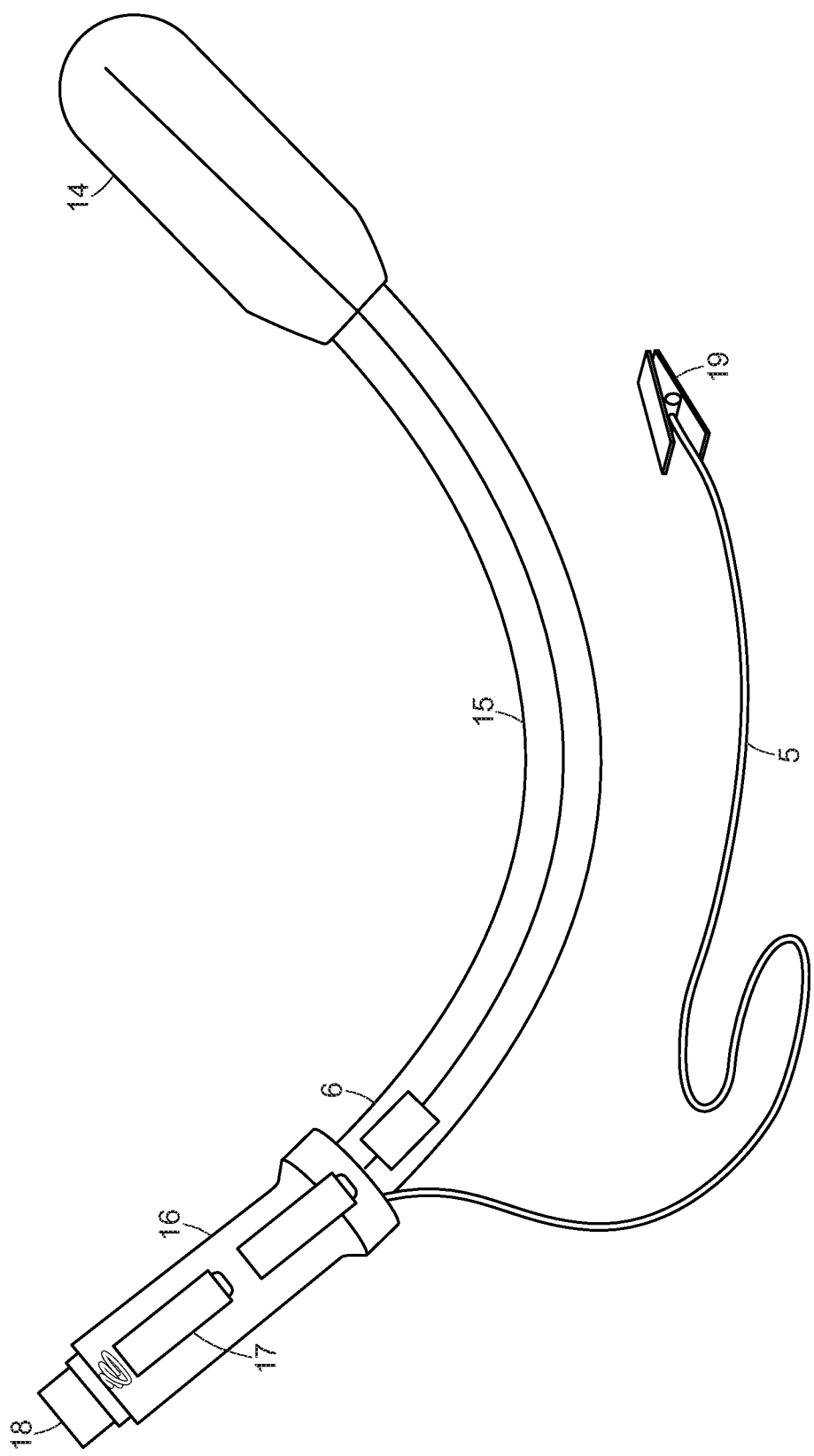
FIG. 2 shows an exemplary vaginal probe in accordance with one or more embodiments, which has a non-conductive handle and shaft that houses the ammeter and a battery compartment, and detachable metallic tips that come in several sizes, which may be placed into and can manipulate the vagina during surgery. A wire that comes off the handle or shaft is connected to the needle driver with an attachment device.

FIG. 2 illustrates the basic design of the vaginal probe, with a metallic vaginal tip (14) that has a conductive surface, a shaft (15), and a handle (16), to which one or more wires (5) may be attached to an ammeter (6) for determination of electrical conductance. The handle (16) may have a compartment for housing batteries (17) that power the ammeter. A light and/or buzzer (18) may be located on the handle or shaft and will indicate when full thickness penetration occurs (i.e., when the needle on the needle driver perforates the condom and makes contact with the metallic distal probe tip). A clip (19) at the end of the wire may be attached to the needle driver.

Having thus described several illustrative embodiments, it is to be appreciated that various alterations, modifications, and improvements will readily occur to those skilled in the art. Such alterations, modifications, and improvements are intended to form a part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Additionally, elements and components described herein may be further divided into additional components or joined together to form fewer components for performing the same functions. Accordingly, the foregoing description and attached drawings are by way of example only, and are not intended to be limiting.

The invention claimed is:

1. An electrical tissue injury detection system comprising:
a probe comprising a shaft, a handle at a proximal end of the shaft, and a delineator at a distal end of the shaft, wherein the delineator is sized and shaped to conform to an interior of a hollow organ, and the delineator includes an electrically conductive tip covered by a non-conducting material;
an electrically conductive surgical tool, said tool capable of piercing the non-conducting material covering the tip of the delineator, wherein the non-conducting material is configured to prevent an electrical circuit from being completed between the electrically conductive surgical tool and the electrically conductive tip of the delineator;
a meter electrically coupled to the probe and the surgical tool, said meter configured to measure an electrical parameter between the probe and the surgical tool and to produce a warning signal when the electrical parameter changes in a manner that indicates perforation of an anatomic structure by the surgical tool; and
a direct current (DC) power source electrically connected to at least one of the probe, the tool, and the meter.

2. The system of claim 1, wherein the non-conducting material covering the tip of the delineator comprises Latex, Santoprene, Neoprene, or Silicone.

3. The system of claim 1, wherein the non-conducting material covering the tip of the delineator comprises a sleeve fitted over the tip.

4. The system of claim 1, wherein the sleeve fitted over the tip comprises a condom or condom-like sheath.

5. The system of claim 1, wherein the non-conducting material covering the tip of the delineator comprises a coating applied over the tip.

6. The system of claim 1, wherein the electrically conductive surgical tool comprises a needle driver including a surgical needle at a distal end thereof.

7. The system of claim 1, wherein the meter and the power source are installed at the handle of the probe.

8. The system of claim 1, further comprising an indicator to provide a visual, auditory, and/or tactile signal to a user when perforation of the anatomic structure by the surgical tool is detected by the meter.

9. The system of claim 1, wherein the meter and the power source are installed at the handle or shaft of the probe.

10. The system of claim 1, wherein the probe is a vaginal probe, and the delineator is sized and shaped to conform to a vaginal interior.

11. The system of claim 1, wherein the probe further comprises a light source.

12. A probe device for detecting anatomic wall penetration and delineation of anatomic structures during surgery, comprising
a shaft having a distal end and a proximal end;
a handle at the proximal end of the shaft;
a delineator at the distal end of the shaft, wherein the delineator is sized and shaped to conform to an interior of a hollow organ, and the delineator includes an electrically conductive tip covered by a non-conducting material, said non-conducting material being pierceable by an electrically conductive surgical tool used in the surgery, wherein the non-conducting material is configured to prevent an electrical circuit from being completed between the electrically conductive surgical tool and the electrically conductive tip of the delineator;
a meter electrically coupled to the probe and the surgical tool, said meter configured to measure an electrical parameter between the probe and the surgical tool and to produce a warning signal when the electrical parameter changes in a manner that indicates perforation of an anatomic structure by the surgical tool; and
a direct current (DC) power source electrically connected to at least one of the probe, the tool, and the meter.

13. The probe device of claim 12, wherein the non-conducting material covering the tip of the delineator comprises Latex, Santoprene, Neoprene, or Silicone.

14. The probe device of claim 12, wherein the non-conducting material covering the tip of the delineator comprises a sleeve fitted over the tip.

15. The probe device of claim 14, wherein the sleeve fitted over the tip comprises a condom or condom-like sheath.

16. The probe device of claim 12, wherein the non-conducting material covering the tip of the delineator comprises a coating applied over the tip.

17. The probe device of claim 12, further comprising an indicator to provide a visual, auditory, and/or tactile signal to a user when perforation of the anatomic structure by the surgical tool is detected by the meter.

18. The probe device of claim 12, wherein the meter and the power source are installed at the handle or shaft of the probe.

19. The probe device of claim 12, wherein the probe is a vaginal probe, and the delineator is sized and shaped to conform to a vaginal interior.

20. The probe device of claim 12, wherein the probe further comprises a light source.

* * * * *